US00PP24078P3

(12) United States Plant Patent
Hurd

(10) Patent No.: US PP24,078 P3
(45) Date of Patent: Dec. 10, 2013

(54) *HIBISCUS* PLANT NAMED 'TIE DYE'

(50) Latin Name: ***Hibiscus* hybrid (L.)**
Varietal Denomination: Tie Dye

(75) Inventor: Kevin A. Hurd, Chicago, IL (US)

(73) Assignee: Walters Gardens Inc., Zeeland, MI (US)

( * ) Notice: Subject to any disclaimer, the term of this patent is extended or adjusted under 35 U.S.C. 154(b) by 95 days.

(21) Appl. No.: 13/385,987

(22) Filed: Mar. 19, 2012

(65) Prior Publication Data

US 2013/0247259 P1 Sep. 19, 2013

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

*Hibiscus* hybrid plant named 'Tie Dye' is a new and distinct cultivar of winter-hardy herbaceous Rose Mallow with an upright, strong well-branched stems producing many flat-faced flowers with deeply-ruffled, dark pink perimeter ring becoming white toward center and a lustrous cherry-red eye in a bull's eye pattern. The foliage is mostly tri-lobed, medium to dark green with limited purple tinting.

1 Drawing Sheet

Botanical classification: *Hibiscus* hybrid (L.).
Variety denomination: 'Tie Dye'.

BACKGROUND AND ORIGIN OF THE PLANT

The present invention relates to the new and distinct hardy, herbaceous, Rose Mallow plant, *Hibiscus* 'Tie Dye' hybridized by Kevin A. Hurd in the summer of 2006 at a nursery in Zeeland, Mich. The new plant, originally labeled #06-310-29, is from a cross between *Hibiscus* 'Fantasia' U.S. Plant Pat. No. 11,853 as the female pod parent times *Hibiscus* 'Fireball' U.S. Plant Pat. No. 13,631 as the male pollen parent. Both parents have a complex mixture of species in them, most likely including the species: *moscheutos, coccineus, laevis.* *Hibiscus* 'Tie Dye' has been propagated both by stem cuttings and tissue culture at the same nursery in Zeeland, Mich. since 2009. The resultant plants have been found to be stable and true to type in successive generations of asexual reproduction.

BRIEF SUMMARY OF THE PLANT

*Hibiscus* 'Tie Dye' differs from its parents as well as all other hardy *hibiscus* known to the applicant in many traits. The nearest comparison plants are *Hibiscus* 'Turn of the Century' (not patented) and *Hibiscus* 'Luna Blush' (not patented). The foliage color of 'Tie Dye' is a medium to dark green compared to the light green of 'Turn of the Century'. The foliage of 'Luna Blush' is ovate and not frequently cleft or lobed like 'Tie Dye'. 'Turn of the Century' is a slow growing plant, whereas 'Tie Dye' is rapid. 'Tie Dye' is taller than both 'Luna Blush' and 'Turn of the Century'. Both the other comparison plants have flowers with petals that have more concentrated pigment on one radial edge and gradually lighten going toward the opposite radial edge in a pinwheel pattern. The flowers of 'Tie Dye' have more intense dark pink petal perimeter showing greater contrast with the concentric rings of white petal centers and cherry-red eyes than both 'Turn of the Century' and 'Luna Blush'.

Compared to the parents, 'Tie Dye' is more upright and less sprawling than 'Fireball', which also has a solid red flower without the white ring of the new plant. Compared to 'Fantasia' the new plant is taller and more branched and the flower of 'Fantasia' is much smaller and more purple colored without the three distinct rings of intense color like a bull's eye pattern. The foliage of 'Fantasia' is smaller with shorter mid lobe, and lighter green than the new plant. The foliage of 'Fireball' is more finely dissected. The flower of 'Fantasia' is more cupped and 'Fireball' less ruffled than 'Tie Dye'.

*Hibiscus* 'Tie Dye' is a unique winter-hardy herbaceous *hibiscus* with the following combined traits:

1. Well-branched, upright habit with strong stems.
2. Many flat-faced flowers with deeply-ruffled, dark pink perimeter becoming white toward center and a lustrous cherry-red eye in a concentric bull's eye pattern.
3. Heterophyllus foliage of medium to dark green mostly tri-lobed leaves with limited purple tinting.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a two-year old plant grown in full sun field in loamy sand soil in trial gardens of a nursery in Zeeland, Mich.

DETAILED BOTANICAL DESCRIPTION

Figure 1:
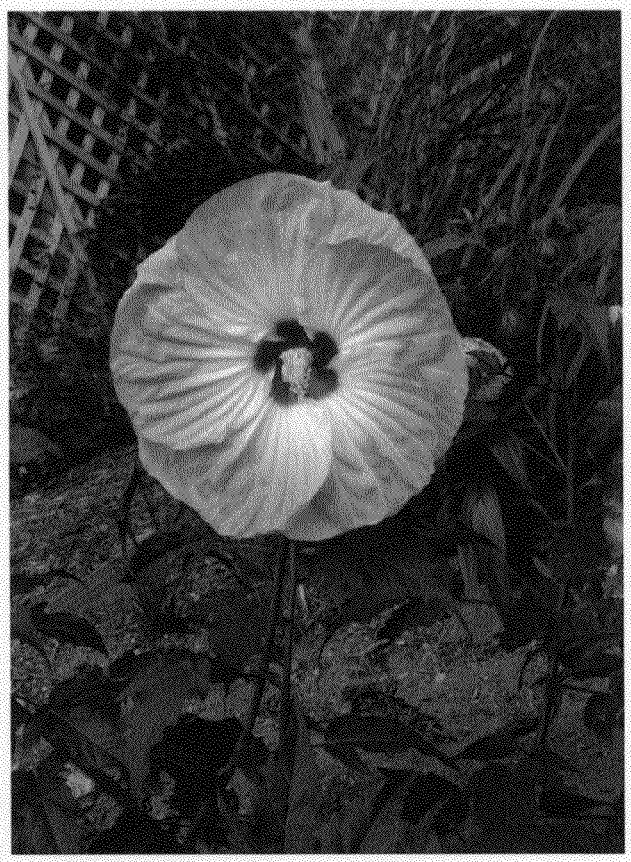
FIG. 1 shows a close-up of the flower with intense, concentric-ring, bull's-eye pattern.
Figure 2:
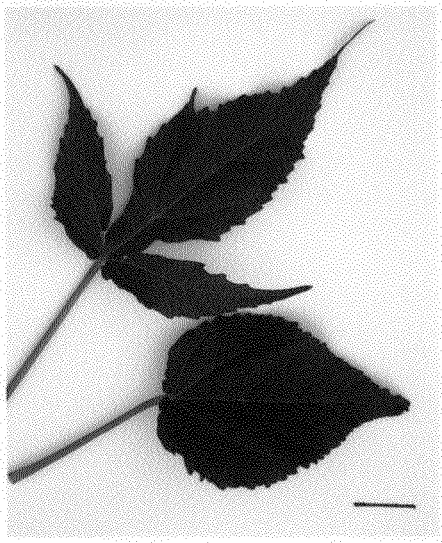
FIG. 2 shows the variable foliage types with the bar in the lower right equal to 2.5 cm.

The following descriptions and color references are based on the 2001 edition of The Royal Horticultural Society Colour Chart except where common dictionary terms are used. The new plant, *Hibiscus* 'Tie Dye', has not been observed under all possible environments. The phenotype may vary slightly with different environmental conditions, such as temperature, light, fertility, moisture and maturity levels, but without any change in the genotype. The following observations and size descriptions are of two-year old plants in the loamy-sand open field trials of a nursery in Zeeland, Mich. with supplemental fertilizer and water as needed, or in the case where significant flower petal color exists, also the specimen was grown at the same nursery location under greenhouse conditions with fertilizer and water but no growth regulators. The plants are grown in natural habit and were not treated with plant growth regulators, nor were they pinched at any time in the growth year to promote additional branching.

Parentage: *Hibiscus* 'Fantasia' U.S. Plant Pat. No. 11,853 (female pod parent) times *Hibiscus* 'Fireball' U.S. Plant Pat. No. 13,631 (male pollen parent).

Propagation:

*Method.*—Stem cuttings and sterile plant tissue culture division.

*Time to initiate roots from tissue culture.*—About two weeks.

*Rooting habit.*—Normal, branching, developing thick to about 4 cm diameter, fleshy; root color creamy white between RHS 159A and lighter than RHS 159 D depending on soil type.

*Crop time.*—Under normal summer growing conditions 12 to 16 weeks to flower in a four-liter container from cutting. Plant vigor is rapid.

Plant description:

*Plant shape and habit.*—Hardy herbaceous perennial with 4 to 8 thick upright and heavily branched main stems producing an upright mound; 10 to 16 primary branches per main stem protruding at about a 45° angle from vertical and curving upward; lateral branch size between 7.5 cm and 25 cm long (shorter at the upper nodes) and 0.3 cm to 1.0 cm diameter at the base of branch.

*Plant size.*—Unpinched plant with stems 100 to 120 cm tall, average about 105 cm tall from soil line, and diameter at base average about 2.0 cm; overall plant 100 to 140 cm wide at the widest point about two thirds height from base.

*Node.*—About 30 per main stem; internode length unpinched plant varied between 2.5 cm to 5.5 cm, average about 3.0 cm.

*Foliage description.*—Alternate; dentate; glabrous; heterophyllous; base equilateral, rounded; mostly palmatifid tri-lobed with clefts open to less than 90 degrees with some immature leaves oblong ovate with rounded bases and acute apexes, texture dull above and below with young expanding leaves starting lustrous; leaf size average 15.5 cm long and 12.5 cm wide, becoming smaller in distal portion of stem; lobes dissected to 4.0 cm to 6.0 cm long segments.

*Foliage color.*—Adaxial side between RHS 139A and RHS 137B with tinting of nearest RHS N186B; abaxial side between RHS 147A and RHS 147B.

*Veins.*—Palmate; ridged below, slightly impressed above.

*Vein color.*—Adaxial primary veins becoming reddish between RHS 185C and RHS 187D with greater light exposure; adaxial secondary and veins with less direct light nearest RHS 138D; primary and secondary abaxial veins nearest RHS 148D.

*Petioles.*—Glabrous; mostly cylindrical; average size 8.0 cm long and 3.5 mm wide; above color between RHS 187D and RHS 45C, more purple when exposed to intense sunlight; abaxial variable combinations of RHS 31D, RHS 37D and RHS 148 D with lower leaves in less light.

Flower description:

*Buds.*—One day prior to opening about 6.5 cm long and 4.0 cm in diameter, acute to rounded apex and bluntly rounded base, unopened petals wrinkled along veins, exposed petal color nearest RHS 67C at perimeter or distal tip, and nearest RHS 62D toward calyx; prior to showing petals buds are about 4.0 cm long and 3.0 cm in diameter, ovoid with sharply acute apex, carinate at the fusion seam of the sepals; color between RHS 144A and RHS 143A with veining and sepal carina tinted RHS N187D.

*Epicalyx.*—Entire, smooth, glabrous, linear with sharply acute apex, curved around sepals; 11 to 12 per flower; 2.5 cm long tapering to base of 2.0 mm wide; adaxial and abaxial color between RHS 141B and RHS 141C with apical tinting of RHS 183C.

*Sepals.*—Five, proximal half connate forming campanulate star-shaped calyx; acute apex; margin entire, edentate; individually about 4.0 cm long and 2.3 cm wide; abaxial color between RHS 144A and RHS 143A and adaxial color nearest RHS 144C; five primary adaxial sepal veins nearest RHS 144D and abaxial same color as surrounding sepal tissue.

*Flowers.*—Solitary, 16 to 20 per main stem without pinching; face opening flat to about 180 degrees; outwardly to slightly upwardly facing; average 23.0 cm across and petals 2.5 cm deep in center, larger in early part of flowering season; outer dark pink ring about 4.0 to 6.0 cm thick, inner near white ring about 3.5 cm to 4.5 cm wide and inner cherry-red eye about 5.5 cm diameter with feathered outer perimeter; persist for one to frequently two days; effective for at least 12 weeks beginning mid July and lasting into October; no detectable fragrance.

*Petals.*—Five; glabrous, lustrous only in center eye, adnate to the androecium, imbricate to about 120% overlapping at widest part (petals completely overlapping the next petal and 20% of the petal in the position two over); shape: rounded; margins entire, edentate; apex rounded; base short claw-like; average 11 cm long and 13 cm wide at widest portion (larger in earlier part of flowering season); petal veins ribbed on back and impressed 3.0 mm to 4.0 mm in front face giving a puckered appearance and adding to petal strength.

*Petal color of greenhouse grown plant.*—Front face nearest RHS 68C and gradually lightening toward center of perimeter ring to RHS 62D; whiter than RHS N155D in center ring and between RHS 46A and RHS 46B in center eye with feathering on outside of eye of nearest RHS 53C; petal back perimeter between RHS 64C and RHS 64D, center portion whiter than RHS N155D with main petal veins of lighter than RHS 65D radiating to near petal edge.

*Petal color of field grown plant.*—Front face outer ring between RHS 63C and RHS 64D, inner near white ring whiter than RHS 155D, inner dark eye nearest RHS 59B with a lighter feathering of RHS 53C; petal back outer ring between RHS 64D and RHS 63D on perimeter ring, whiter than RHS N155D in center and inner eye nearest RHS 59B.

*Petal veins.*—Diadromous, impressed on front side and ribbed on back side from apex nearly to center eye producing ruffled effect.

*Petal vein color.*—Front face: starting in cherry-red eye: RHS 59B, extending with the feathering into white center with RHS 53C; matching the white ring in center portion and continuing whiter than RHS N155D into outer perimeter ring toward the outer margin matching the perimeter dark pink ring with between RHS 63C and RHS 64D; back face starting in eye: nearest RHS 59B, whiter than RHS N155D extending through the center and into perimeter, and in the outer 2.5 cm between RHS 64D and RHS 63D.

*Gynoecium.*—Style enclosed in column that is average 6.0 cm long and 1.0 cm wide at base; column color lighter than RHS 155D; distal 8.0 mm to 10.0 mm portion of style split into five branches and protrudes from column, branch diameter 2.0 mm, branch color nearest RHS 155D.

*Stigma.*—Five; globose flattened on top, puberulose, about 3 mm in diameter, nearest RHS 158A.

*Ovary.*—About 1.0 cm across at time of flower opening; color between RHS 145D and RHS 150D.

*Androecium.*—Filaments: numerous, about 150; less than 0.5 mm in diameter and about 6.0 mm long; attached to nearly the entire length of column; nearest RHS 155D.

*Anthers.*—Reniform; dorsifixed; about 2.0 mm long and 1.0 mm wide; nearest RHS 11D.

*Pollen.*—Numerous, globose, less than 0.1 mm long, nearest RHS 155B.

*Pedicel.*—Glabrous, rounded; from base of sepal to abscission point average 1.4 cm long and 4.0 mm wide on early lower flowers decreasing in distal flowers; color between RHS 138A and RHS 138B.

*Peduncle.*—Glabrous, rounded; flowers are easily visible, held out on average 5.5 cm long from abscission point to stem and 4.0 mm wide on early flowers shortening to about 4.0 cm higher on stem; color variable between RHS 182A, RHS 148C with stippling of RHS 182A and RHS 185A.

*Fruit.*—Few, loculicidal capsule; glabrous; globose, occasionally with abruptly acute apex; RHS N199B when mature.

*Seed.*—Minutely floccose, globose to slightly reniform; 3 to 4 mm in diameter; RHS 200A.

Disease resistance: Resistance beyond that of other hardy *hibiscus* cultivars has not been observed. The plant grows best with plenty of moisture and adequate drainage, but is able to tolerate some drought when mature.

Hardiness at least from USDA zone 4 through 9, and other disease resistance is typical of that of other *hibiscus* cultivars. The flowers are able to withstand significantly more wind and sun than the typical flat petals of other *hibiscus*.

I claim:

1. A new cultivar of winter-hardy herbaceous *Hibiscus* hybrid plant named 'Tie Dye' as herein illustrated and described, comprising a well-branched, upright habit with strong stems; many flat-faced flowers with deeply-ruffled, dark pink perimeter ring becoming white toward center and a lustrous cherry-red eye in a bull's eye pattern, having mostly tri-lobed medium to dark green leaves suitable for landscaping as a specimen, group or en masse.

* * * * *